US011534286B1

(12) United States Patent
Rayhanabad (10) Patent No.: US 11,534,286 B1
(45) Date of Patent: Dec. 27, 2022

(54) METHOD OF USING AN ENDOVASCULAR STENT-GRAFT WITH AN EXTRA VASCULAR EXTENSION

(71) Applicant: Simon B. Rayhanabad, Huntington Beach, CA (US)

(72) Inventor: Simon B. Rayhanabad, Huntington Beach, CA (US)

(*) Notice: Subject to any disclaimer, the term of this patent is extended or adjusted under 35 U.S.C. 154(b) by 0 days.

(21) Appl. No.: 17/399,811

(22) Filed: Aug. 11, 2021

Related U.S. Application Data (60) Provisional application No. 63/064,320, filed on Aug. 11, 2020.

(51) Int. Cl.
| | | |
|---|---|---|
| *A61F 2/07* | (2013.01) |
| *A61B 17/34* | (2006.01) |
| *A61F 2/06* | (2013.01) |
| *A61M 1/36* | (2006.01) |
| *A61M 27/00* | (2006.01) |
| *A61B 17/00* | (2006.01) |
| *A61B 17/11* | (2006.01) |

(52) U.S. Cl.
CPC ............ *A61F 2/07* (2013.01); *A61B 17/3468* (2013.01); *A61B 2017/00252* (2013.01); *A61B 2017/00557* (2013.01); *A61B 2017/00778* (2013.01); *A61B 2017/1107* (2013.01); *A61F 2002/065* (2013.01); *A61F 2002/075* (2013.01); *A61F 2002/077* (2013.01); *A61F 2220/0075* (2013.01); *A61F 2250/0003* (2013.01); *A61M 1/3655* (2013.01); *A61M 27/002* (2013.01); *Y10S 623/903* (2013.01)

(58) Field of Classification Search
CPC ............... A61F 2/07; A61F 2220/0075; A61F 2250/003; A61F 2002/065; A61B 2017/00252; A61B 2017/00778; A61M 1/3655; A61M 27/002; Y10S 623/913
See application file for complete search history.

(56) References Cited

U.S. PATENT DOCUMENTS

| | | | | |
|---|---|---|---|---|
| 6,140,452 A * | 10/2000 | Felt | .......................... | A61L 27/18 528/65 |
| 9,724,186 B2 * | 8/2017 | Chobotov | .................. | A61F 2/07 |
| 2002/0156150 A1 * | 10/2002 | Williams | ................. | A61L 31/16 523/113 |
| 2010/0204783 A1 * | 8/2010 | Nugent | ..................... | A61F 2/06 623/1.41 |

(Continued)

FOREIGN PATENT DOCUMENTS

WO WO-2006065966 A2 * 6/2006 ......... A61B 17/0218

*Primary Examiner* — Brian E Pellegrino
(74) *Attorney, Agent, or Firm* — Steven R. Vosen (57) ABSTRACT

An endovascular stent-graft with an extravascular extension is presented including: a stent-graft having an aperture and a vascular graft having an and attached to the aperture and a free end. Methods of using the endovascular stent-graft with an extravascular extension include providing the endovascular stent-graft with an extravascular extension to a target vessel of the patient and using free end to either provide access for a circulatory medical procedure or attaching the free end to another point in the circulatory system to perform a bypass operation or to provide a graft for providing hemodialysis. The methods may be performed noninvasively through incisions in the back of the patient.

15 Claims, 5 Drawing Sheets

(56) References Cited

U.S. PATENT DOCUMENTS

2011/0313504 A1\* 12/2011 Golding .................... A61F 2/07
  623/1.11
2015/0142030 A1\* 5/2015 Mactaggart ...... A61B 17/32037
  606/167

\* cited by examiner

METHOD OF USING AN ENDOVASCULAR STENT-GRAFT WITH AN EXTRA VASCULAR EXTENSION

CROSS-REFERENCE TO RELATED APPLICATIONS

This application claims the benefit of U.S. Provisional Application No. 63/064,320, filed Aug. 11, 2020, the contents of which are hereby incorporated by reference in its entirety.

BACKGROUND OF THE INVENTION

Field of the Invention

The present invention generally relates to medical devices, and more particularly to an endovascular stent-graft with an extravascular extension and a method of providing an endovascular stent-graft with an extravascular extension to a patient.

Discussion of the Background

There are a variety of surgical procedures, such as those that require access to the aorta, or vena cava, which requires a surgeon to access these blood vessels through the abdomen or the chest. Thus, for example, coronary bypass surgery, in which blood flow is redirected around a section of a blocked or partially blocked artery, is performed by making a long incision in the chest, cutting the center of the chest along the breastbone, spreading the rib cage open to expose the heart, and inserting a healthy blood vessel, often from inside the chest wall or from the lower leg by attaching the ends above and below the blocked artery so that blood flow is redirected around the narrowed part of the diseased artery. Such procedures are highly invasive.

On the other hand, there are several procedures that access the heart, but which are much less invasive, such as coronary stent placement. This procedure is performed with a stent delivery apparatus in which a compressed, self-expanding stent is placed in the tip at a distal end of a delivery system. The tip is then inserted into an artery in the groin, arm or wrist area and is directed through the artery and towards the heart. Once the tip reaches the required location, the delivery system is actuated, releasing the compressed stent in the artery, which then expands to sit against the inner walls of the artery near the heart, and the delivery system is removed.

Unfortunately, devices used for such non-invasive procedures are not useful for preforming more complicated procedures, such as coronary bypass surgery.

There is a need in the art for less invasive surgical procedures and for medical devices that support such procedures. In addition, to coronary bypass procedures, such devices should also be useful in procedures that involve other large blood vessels, such as the vena cava, iliac, or common femoral artery.

BRIEF SUMMARY OF THE INVENTION

The present invention overcomes the disadvantages of prior art by providing an endovascular stent-graft having an extravascular extension, also referred to herein, without limitation, as an "stent-graft with branching graft."

It is one aspect of certain embodiments to provide a stent-graft with branching graft including: a stent-graft having a first end, a second end, and an aperture through the stent-graft between the first end and the second end, and a vascular graft having a first end and a second end, where the first end of the vascular graft extends from the aperture of the stent-graft, where a lumen of the stent-graft with branching graft includes a lumen of the sent-graft and a lumen of the vascular graft.

It is another aspect of certain embodiments to provide a method of using a stent-graft with branching graft to perform a medical procedure, where the stent-graft with branching graft includes a stent-graft having a first end, a second end, and an aperture through the stent-graft between the first end and the second end, and a vascular graft having a first end and a second end, where the first end of the vascular graft extends from the aperture of the stent-graft, and where a lumen of the stent-graft with branching graft includes a lumen of the sent-graft and a lumen of the vascular graft. The method includes: incising the skin of the patient to form an incision; puncturing the target vessel of the patient with a needle; providing the stent-graft through the incision, through the puncture of the target vessel, and into the lumen of the target vessel; and expanding the stent-graft such that the stent-graft contacts an inner surface of the target vessel, such that the stent-graft is within the target vessel and such that the vascular graft extends out of the target vessel through the puncture.

In certain embodiments, the method provides access to the circulatory system of the patient through the vascular graft, and providers for performing medical procedures on the circulatory system.

In certain other embodiments, the target vessel is a vena cava of the patient, and the method provides a graft for performing hemodialysis.

These features together with the various ancillary provisions and features which will become apparent to those skilled in the art from the following detailed description, are attained by the endovascular stent-graft with an extravascular extension and method of the present invention, preferred embodiments thereof being shown with reference to the accompanying drawings, by way of example only, wherein:

Reference symbols are used in the Figures to indicate certain components, aspects or features shown therein, with reference symbols common to more than one Figure indicating like components, aspects or features shown therein.

DETAILED DESCRIPTION OF THE INVENTION

The following description includes the disclosure of an endovascular stent-graft and several minimally invasive interventions enabled by the endovascular stent-graft. In general, as described subsequently, the endovascular stent-graft includes a stent-graft and a vascular graft that branches from the stent-graft and forms an extravascular extension.

The endovascular stent-graft with an extravascular extension may be inserted into the body near, for example, the aorta, iliac, or femoral areas, and through an incision in a target vessel, such as an artery or vein, and with the graft extending through the incision to the outside of the target vessel. The graft then provides access to the circulatory system.

Figure 1:
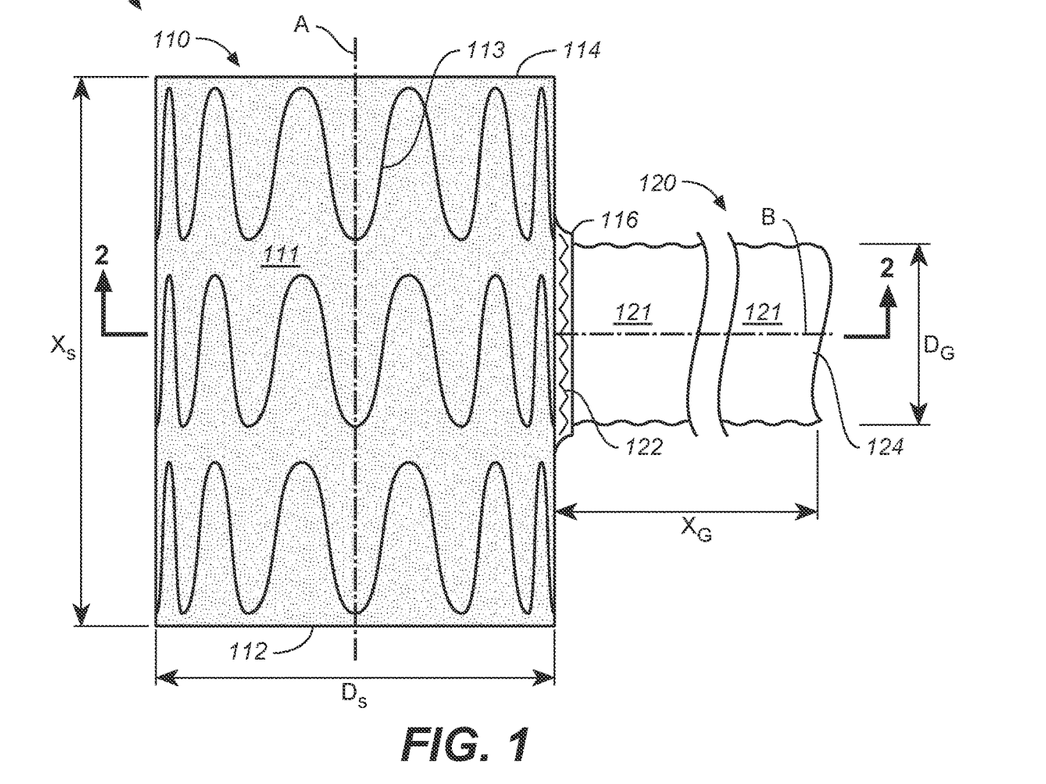
FIG. 1 is a side view of a first embodiment endovascular stent-graft.
Figure 2:
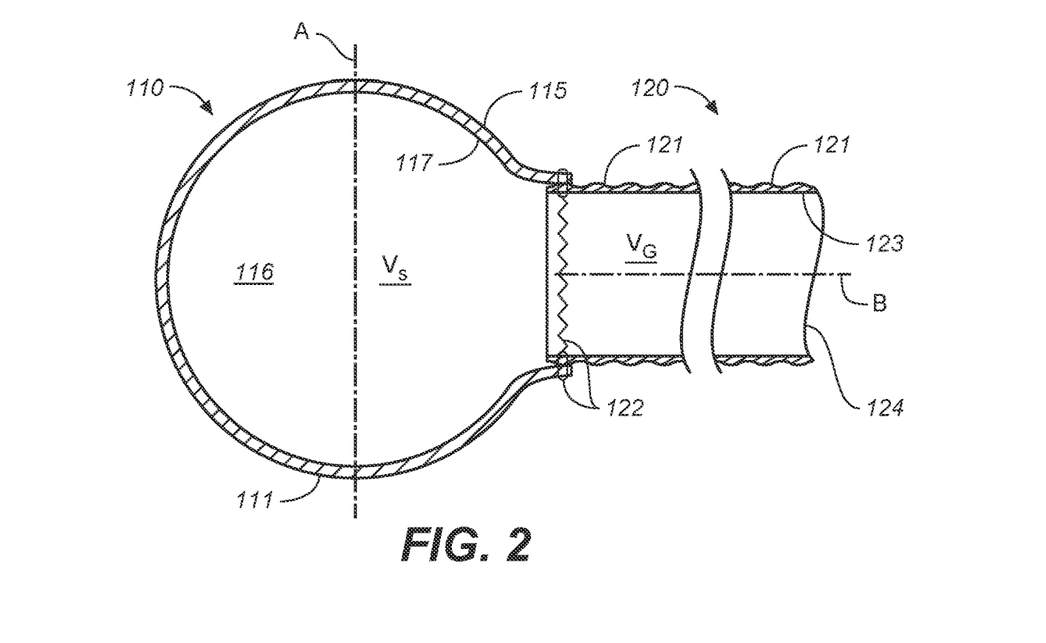
FIG. 2 is a sectional top view 2-2 of FIG. 1.

FIG. 1 is a side view of a first embodiment endovascular stent-graft 100 and FIG. 2 is a sectional top view 2-2 of FIG. 1. Endovascular stent-graft 100 includes a stent-graft 110 and a branching vascular graft 120.

Stent-graft 110 has an outer surface 115 and an inner surface 117 and includes a stent 113, which is a metal framework or mesh, covered by a graft 111, which is a thin fabric formed from a polyester, such as expanded polytetrafluoroethylene (ePTFE). Stent 113 of stent-graft 110 is a collapsible and self-expanding structure formed from a metal alloy such as nickel titanium, which also known as nitinol, and graft 111 of the stent-graft is a barrier to the flow fluids, such as blood.

The expanded shape of stent-graft 110 is generally cylindrical, with a centerline A, a diameter Ds, and a length, Xs, between a first end 112 and a second end 114, and a lumen Vs. Stent-graft 110 differs from commercially available stent-grafts in that it includes an aperture 116. As discussed subsequently, the shape of aperture 116 matches that vascular graft 120. In certain embodiments, aperture 116 is located midway between first end 112 and second end 114, as shown in the Figures. In certain other embodiments, aperture 116 is closer to one of first end 112 or second end 114.

Vascular graft 120 has an outer surface 121 and an inner surface 123, and is generally cylindrical and extends from a first end 122 to a second end 124. The material of vascular graft 120 may, for example and without limitation, be ePTFE. Vascular graft 120 is generally cylindrical in shape, with a centerline B, diameter Dg, and a length, Lg, between first end 122 and second end 124, and a lumen $V_G$.

First end 112 of vascular graft 120 extends from aperture 116, such that a lumen of the endovascular stent-graft 100 includes a lumen of the stent-graft 110 and a lumen of the vascular graft 120. In one embodiment, first end 116 is joined to aperture 116 of stent-graft 110 by a suture 121, by which may be a conventional medical suture. In other embodiments, stent-graft 110 and branching vascular graft 120 are joined by bonding, such a by an adhesive, or are formed as a single piece in the manufacturing process.

In certain embodiments, it is preferred that the portion of sent-graft 110 near aperture 116 includes a sufficient amount of stent 113 material so as to provide an outwards radial force so that the stent-graft maintains the circular shape of the aperture.

In certain embodiments, the diameter of stent-graft 110, Ds, is from 1 to 5 cm, the length of the stent-graft, Ls, is from 15 to 40 cm. Typically, the diameter Ds is selected to be slightly larger that the target vessel into which is to be inserted. The diameter of vascular graft 120, Dg, is from 5 to 10 cm, and the length of vascular graft 120, Lg, is from 3 to 70 cm.

By way of example, a commercially available stent-graft which is similar to stent-graft 110 is, without limitation, a GORE® VIABAHN® VBX Balloon Expandable Endoprosthesis (see https://www.goremedical.com/products/vbx), manufactured by W. L. Gore & Associates, Inc. (Newark, Del.). Further, by way of example, a commercially available grafts which is similar to vascular graft 120 is, without limitation, a GORE-TEX® Stretch Vascular Graft (see https://www.goremedical.com/products/vgstretch), manufactured by W. L. Gore & Associates, Inc. (Newark, Del.).

Figure 3:
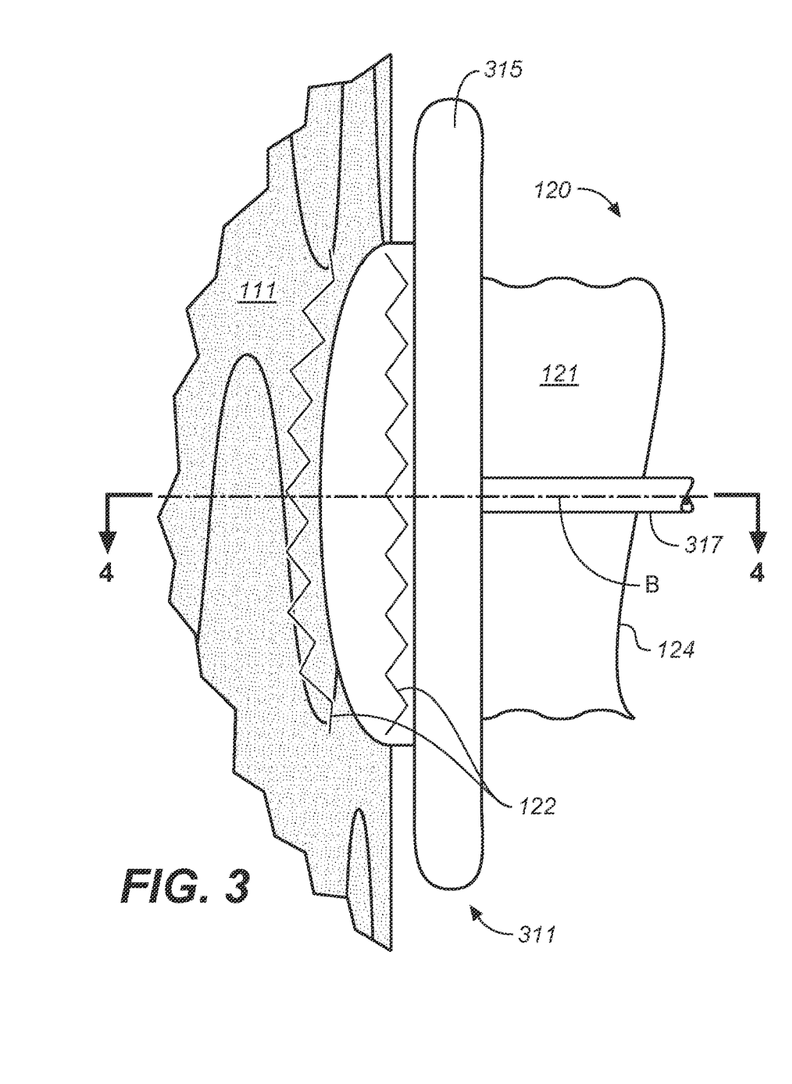
FIG. 3 is a side view of a portion of a second embodiment endovascular stent-graft.
Figure 4:
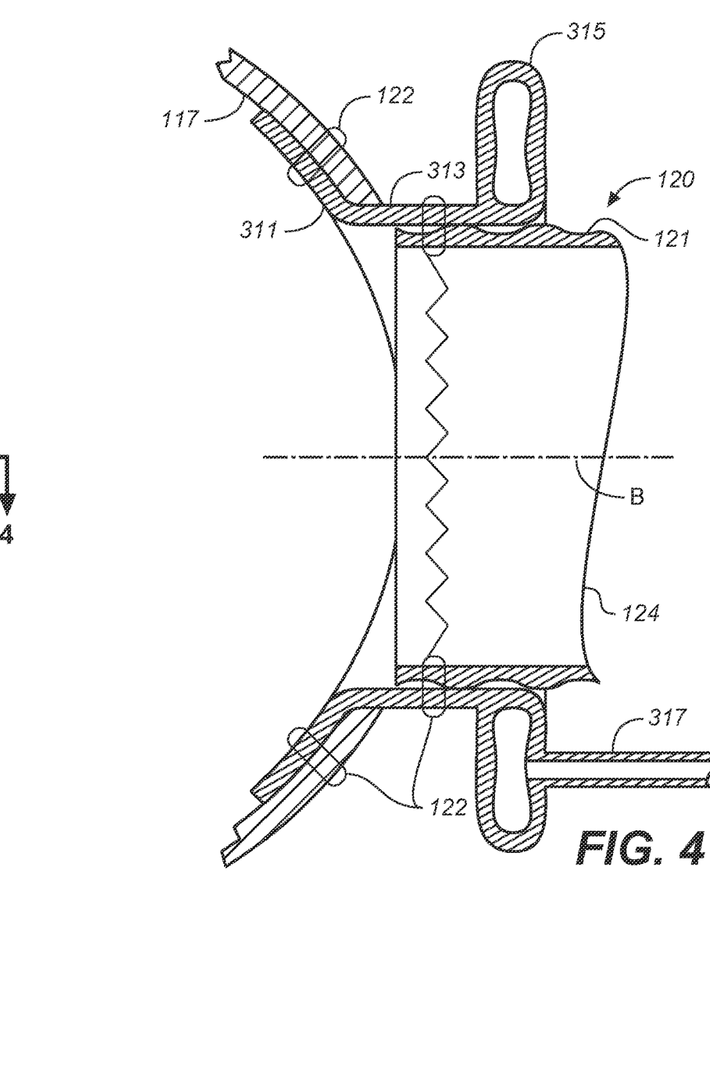
FIG. 4 is a sectional top view 3-3 of FIG. 3.

FIG. 3 is a detailed side view of a second embodiment endovascular stent-graft 300 and FIG. 4 is a sectional top view 4-4 of FIG. 3. Endovascular stent-graft 300 is generally similar to endovascular stent-graft 100, except as explicitly noted.

Endovascular stent-graft 300 includes stent-graft 110 and graft 120, as discussed above, and also includes a sealing assembly 310 including a first portion 311 attached to inner surface 115 of graft 111, a second portion 313 attached to outer surface 123 of vascular graft 120, a balloon 315, and a tube 317 in fluid communication with the balloon and which is used for inflating/deflating the balloon. An end of tube 317 that is not attached to balloon 315 may be attached to a pump and/or a sealing mechanism to maintain inflation of the balloon. First portion 311 and inner surface 115, and second portion 313 and outer surface 123 are attached, for example and without limitation, with suture 122. Alternative, one or both of these attachments may be manufactured as one piece. Balloon 315 may be inflated using tube 317 to force the balloon is against graft 111.

Endovascular stent-graft 100 or 300 may be used for any one of a number of procedures the require access to the circulatory system including, but not limited to, bypassing the aorta, bypassing the distal iliac-femoral-popliteal bypass, providing dialysis grafts, and providing access to the heart for certain medical procedures.

The first steps of using endovascular stent-graft 100 and 300 is to deliver stent-graft 110 of the endovascular stent-graft into the target vessel. Stent-graft 110 is generally similar to conventional stent-grafts, and may utilize conventional stent-graft delivery systems. One example of a stent-graft delivery system is, without limitation, a Valiant Thoracic Stent-graft with the Captivia Delivery System (https://www.medtronic.com/us-en/healthcare-professionals/products/cardiovascular/aortic-stent-grafts/valiant-thoracic-stent-graft-with-captivia-delivery-system.html), manufactured by Medtronic (Fridley, Minn.).

Thus, for example, stent-graft 110 is compressed and provided into the tip of the delivery system (not shown). Next, a surgeon makes an incision of the patient's body, directs a need to the location in the target vessel where the endovascular stent-graft 100 or 300 is to be delivered, and punctures the target vessel with the needle. In certain embodiments, the patient is placed on their abdomen and the first incision is made through the patient's back using a trans-lumbar approach.

Next, the surgeon inserts a guide wire through the needle and into the target vessel, and then removes needle leaving the guide wire in place.

Next, the dilator and sheath are passed together, over the guide wire, and into the blood vessel, where the tapered tip of the dilator acts to stretch the opening in the blood vessel to allow for the insertion of the larger sheath. The dilator is then removed, leaving only the sheath and guide wire in blood vessel, where the sheath provides a port into the blood vessel.

Next, the surgeon guides the tip of the delivery system, with or without the aid of a computerized tomography (CT) scan, through the sheath and into the target vessel. With the compressed stent-graft 110 inside the target vessel, and with vascular graft 120, and optionally tube 317, extending outside of the target vessel, the surgeon operates the delivery system to release stent-graft 110, and then removes the delivery system from the patient.

Figure 5A:
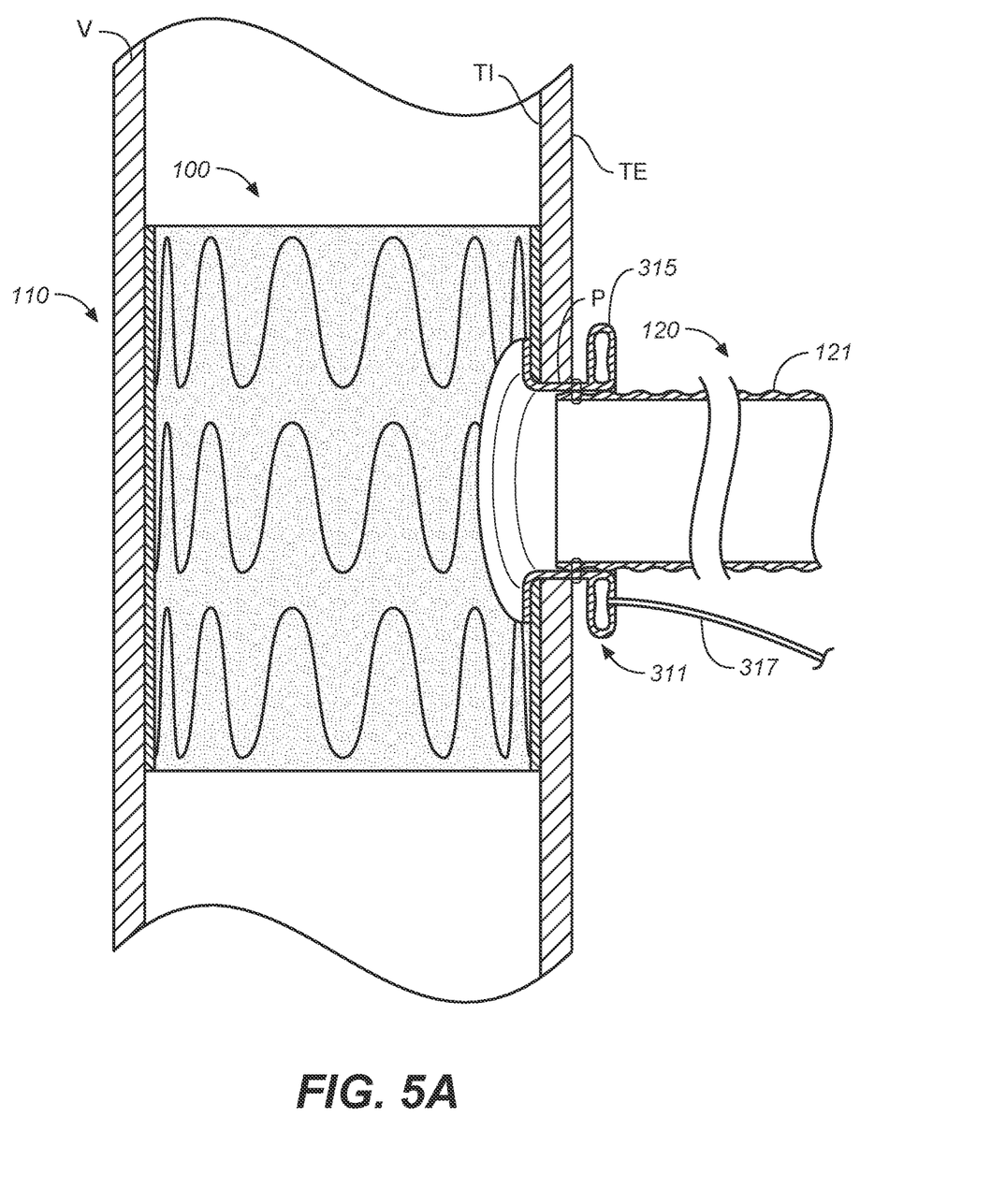
FIGS. 5A and 5B are a first and second side view, respectively, illustrating the placement of the second embodiment endovascular stent-graft in a target vessel.
Figure 5B:
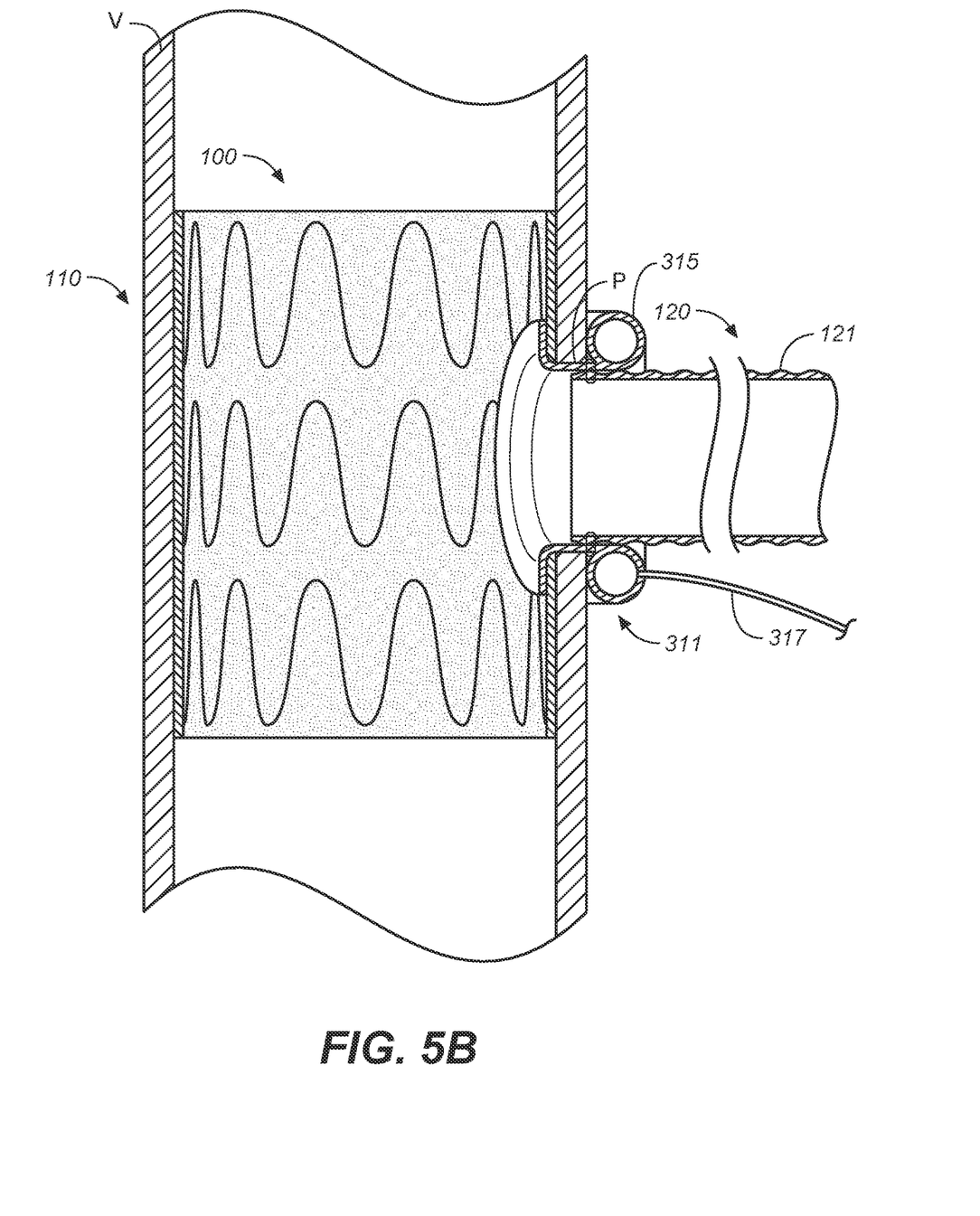

Placing endovascular stent-graft with an extravascular extension 300 requires an extra step, as illustrated for example in FIGS. 5A and 5B, which are a first and second side view, respectively, illustrating the placement of the endovascular stent-graft 300 in a target vessel, V.

FIG. 5A illustrates the initial placement of endovascular stent-graft with an extravascular extension 300 in a target blood vessel, V, having a tunica intima, TI, and a tunica externa, TE. The expanded stent-graft 110 contacts tunica intima, TI with vascular graft 120 extending though a puncture P of target vessel, V. This figure also illustrates the placement of an expanded endovascular stent-graft with an extravascular extension 100 in target vessel, V.

In a next step, FIG. 5B illustrates the use of tube 317 to inflate balloon 315. A portion of balloon 315 expands towards and provides a force against tunica externa, TE, compressing target vessel, V, between the balloon and stent-graft 110. The resulting compression force acts to secure endovascular stent-graft 300 to the target vessel, V, and reduce the likelihood of a leak of blood from the target vessel.

Once stent-graft 110 of endovascular stent-graft 100 or 300 is released from the delivery system, the stent-graft expands and seats against the inner surface of target vessel. At this time, endovascular stent-graft 100 or 300 is in place, and vascular graft 120 is either attached to a second target vessel or uses the graft to access the circulatory system, as described subsequently.

Several specific uses of endovascular stent-graft with an extravascular extension 100 or 300 are now presented. These uses are illustrative and are not meant to limit the scope of the present invention. The first steps are those discussed above, which describe the placement of the endovascular stent-graft with an extravascular extension in the target vessel. If length Lg of vascular graft 120 is not sufficient for the intended use of endovascular stent-graft with an extravascular extension 100 or 300. Then an additional length of graft may be sutured to end 124, effectively increasing the length of lumen of the vascular graft.

Figure 6:
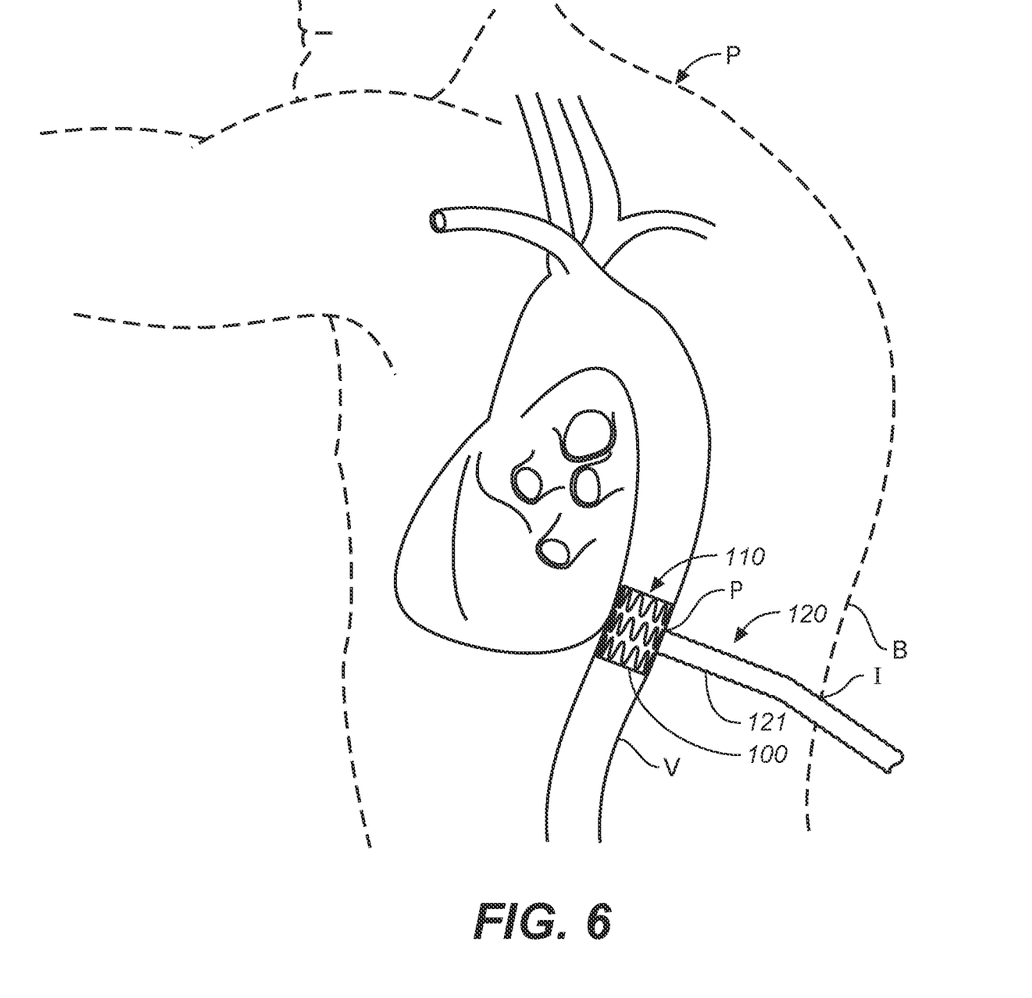
FIG. 6 illustrates one use of the endovascular stent-graft.

A first use of endovascular stent-graft with an extravascular extension 100 or 300 is to allow external access to the heart, for example, to perform a heart valve repair procedure, as illustrated in FIG. 6, which illustrates the use of the method on a patient P have a back B and an artery (for example aorta or vena cava). FIG. 6 also shows the location of a site of an incision, I, in the patient's back and the puncture, P, in the target vessel V. Once endovascular stent-graft with an extravascular extension 100 or 300 is in place in target vessel V, the second end 124 of vascular graft 120 is left open and external to the patient. The surgeon then inserts devices for providing minimally invasive surgery, as are known in the art, into send end 124, through the aorta or vein, and to the heart. Once the heart valve is repaired and the device for effecting the repair are removed from endovascular stent-graft 100 or 300, vascular graft 120 is tied off and incision I is sutured. This method has the advantage over the prior art in that the surgeon minimally invasively enters the patent through their back.

A second use of endovascular stent-graft 100 or 300 is for a aortobifemoral bypass. For this use, the target vessel is an artery, and the second end 124 of vascular graft 120 is attached elsewhere in the circulatory system of the patient, such as the leg, to provide a bypass. Once endovascular stent-graft 100 or 300 is thus placed, incision I is sutured. This method has the advantage over the prior art, where the surgeon accesses the target vessel though the abdomen, in that the surgeon minimally invasively enters the patient through their back.

A third use of endovascular stent-graft 100 or 300 is for hemodialysis. For this use, the target vessel is the vena cava the second end 124 of vascular graft 120 is attached, under the skin, to the femoral artery. Once endovascular stent-graft 100 or 300 is thus placed, incision I is sutured. Dialysis is then provided using vascular graft 120, which is located under the skin.

A fourth use of endovascular stent-graft 100 or 300 is to provide access to the aorta for any intra-aortic procedure when the lower part of the aorta is blocked.

A fifth use of endovascular stent-graft 100 or 300 is to bypass blockages in the iliac or femoral arteries to the popliteal artery.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment. Furthermore, the particular features, structures or characteristics may be combined in any suitable manner, as would be apparent to one of ordinary skill in the art from this disclosure, in one or more embodiments.

Similarly, it should be appreciated that in the above description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

I claim:

1. A method of using a stent-graft with branching graft to perform a medical procedure, where the stent-graft with branching graft includes a stent-graft having a first end, a second end, and an aperature through the stent-graft between the first end and the second end, and a vascular graft having a first end and a second end, where the first end of the vascular graft is attached to the aperture of the stent-graft and where the second end of the vascular graft extending away from the aperature of the stent-graft, and where a lumen of the stent-graft with branching graft includes a lumen of the sent-graft and a lumen of the vascular graft the method comprising:

incising the skin of the patient's back to form an incision;
  puncturing the target vessel of the patient with a needle to form an opening in the target vessel;
  providing the stent-graft through the incision, through the opening in the target vessel, and into the lumen of the target vessel, and
  expanding the stent-graft such that the stent-graft contacts an inner surface of the target vessel,
  such that the stent-graft is within the target vessel, such that the vascular graft extends out of the target vessel through the opening to provide access to the interior of the target vessel through the patient's back.

2. The method of claim 1, where the aperture through the stent-graft is midway between the first end of the stent-graft and the second end of the stent-graft.

3. The method of claim 1, where the aperture through the stent-graft is closer to the first end of the stent-graft than to a location midway between the first end of the stent-graft and the second end of the stent-graft.

4. The method of claim 1, where the first end of the vascular graft is sutured to the aperture of the stent-graft.

5. The method of claim 1, where the diameter of the stent-graft is from 1 to 5 cm.

6. The method of claim 1, where the length of the stent-graft is from 15 to 40 cm.

7. The method of claim 1, where the diameter of the vascular graft is from 5 to 10 cm.

8. The method of claim 1, where the length of the vascular graft is from 3 to 70 cm.

9. The method of claim 1, further comprising a sealing assembly including an inflatable balloon attached to and extending circumferentially around the vascular graft such that when the inflatable balloon is inflated, the balloon contacts an outer surface of the target vessel.

10. The method of claim 1, where the target vessel is an artery or a vein.

11. The method of claim 10, where the target vessel is an aorta of the patient, where the lower part of the aorta is blocked, and where the medical procedure is an intracortical procedure.

12. The method of claim 1, where the stent-graft with branching graft further includes a sealing assembly including an inflatable balloon attached to and extending circumferentially around the vascular graft near the aperture of the stent-graft, said method further comprising:
inflating the balloon such that the balloon contacts an outer surface of the target vessel.

13. The method of claim 1, further comprising:
guiding a surgical instrument through the second end of the vascular graft, into the target vessel, and into a circulatory system of the patient;
performing a medical procedure within in the circulatory system of the patient;
removing the surgical instrument from the patient;
sealing the vascular graft to prevent fluid from escaping from the target vessel; and
sealing the incision.

14. The method of claim 13, where the surgical procedure is performed on a heart of the patient.

15. The method of claim 1, where the target vessel is an artery, and where the method is an aortobifemoral bypass and includes:
attaching the second end of the vascular graft to a location in a circulatory system of the patient; and
sealing the incision.

\* \* \* \* \*